United States Patent
Sandler

(10) Patent No.: US 10,570,373 B2
(45) Date of Patent: Feb. 25, 2020

(54) POST-NATAL HEMATOPOEITIC ENDOTHELIAL CELLS AND THEIR ISOLATION AND USE

(71) Applicant: CORNELL UNIVERSITY, Ithaca, NY (US)

(72) Inventor: Vladislav M. Sandler, New York, NY (US)

(73) Assignee: Cornell University, Ithica, NY (US)

( * ) Notice: Subject to any disclaimer, the term of this patent is extended or adjusted under 35 U.S.C. 154(b) by 93 days.

(21) Appl. No.: 15/032,287

(22) PCT Filed: Nov. 13, 2014

(86) PCT No.: PCT/US2014/065469
§ 371 (c)(1),
(2) Date: Apr. 26, 2016

(87) PCT Pub. No.: WO2015/073680
PCT Pub. Date: May 21, 2015

(65) Prior Publication Data
US 2016/0251622 A1 Sep. 1, 2016

Related U.S. Application Data

(60) Provisional application No. 61/956,194, filed on Nov. 13, 2013.

(51) Int. Cl.
*C12N 5/0789* (2010.01)
*A01N 1/02* (2006.01)
*A61K 35/28* (2015.01)
*G01N 33/569* (2006.01)
*C12N 5/071* (2010.01)

(52) U.S. Cl.
CPC .......... *C12N 5/0647* (2013.01); *A01N 1/0221* (2013.01); *A61K 35/28* (2013.01); *C12N 5/069* (2013.01); *G01N 33/56966* (2013.01); *C12N 2501/125* (2013.01); *C12N 2501/145* (2013.01); *C12N 2501/2303* (2013.01); *C12N 2501/2306* (2013.01); *C12N 2501/26* (2013.01); *G01N 2333/70596* (2013.01); *G01N 2333/916* (2013.01)

(58) Field of Classification Search
None
See application file for complete search history.

(56) References Cited

U.S. PATENT DOCUMENTS

2005/0163760 A1   6/2005   Cartier-Lacave et al.

FOREIGN PATENT DOCUMENTS

| WO | 2013075222 | 5/2013 |
| WO | 2013116307 | 8/2013 |

OTHER PUBLICATIONS

Extended Search Report for corresponding EP Application No. 14861900.0, European Patent Office, dated Apr. 18, 2017.
E. Oberlin et al., :VE-cadherin expression allows identification of a new class of hematopoietic stem cells within human embryonic liver, Blood Journal, vol. 116, No. 22, pp. 4444-4455, Aug. 6, 2010.
StemSite Portal: The Transcriptional Landscape of Hematopoietic Stem Cell Ontogeny; http://daleystem.hms.harvard.edu/; Apr. 19, 2016.
North, T. E. et al., "Runx1 Expression Marks Long-Term Repopulating Hematopoietic Stem Cells in the Midgestation Mouse Embryo", Immunity 16:661-672 , May 2002.
de Bruijn, M. F. et al., "Definitive hematopoietic stem cells first develop within the major arterial regions of the mouse embryo" The EMBO Journal, vol. 19, No. 11, pp. 2465-2474, 2000.
Medvinsky, A. et al., "Definitive Hematopoiesis is Autonomously Initiated by the AGM Region", Cell, vol. 86, 897-906, Sep. 20, 1996.
Zovein, A. C. et al. Cell Stem Cell, "Fate Tracing Reveals the Endothelial Origin of Hematopoietic Stem Cells" 3:625-636, Dec. 4, 2008.
Boisset, J. C. et al., "In vivo imaging of haematopoietic cells emerging from the mouse aortic endothelium", Nature 464:116-120, Mar. 4, 2010.
Bertrand, J. Y. et al., Nature, "Haematopoietic stem cells derive directly from aortic endothelium during development", vol. 464, pp. 108-111, Feb. 14, 2010.
Kissa, K. et al., Nature, "Blood stem cells emerge from aortic endothelium by a novel type of cell transition", vol. 464, pp. 112-115, Feb. 14, 2010.
Chen, M. J. et al., Nature, "Runx1 is required for the endothelial to haematopoietic cell transition but not thereafter", vol. 457, pp. 887-891, Jan. 7, 2009.
North, T. E. et al., Cell, "Hematopoietic Stem Cell Development is Dependent on Blood Flow", vol. 137, pp. 736-748, May 13, 2009.
Kim et al., Blood, "CD144 (VE-cadherin) is transiently expressed by fetal liver hematopoietic stem cells", vol. 106, pp. 903-905, Apr. 14, 2005.
Wu et al., "Hemogenic endothelial progenitor cells isolated from human umbilical cord blood." Stem Cells, vol. 25, pp. 2770-2776, Jul. 19, 2007.
De Golovine et al., "Goldenhar syndrome: a cause of secondary immunodeficiency?" Allergy Asthma Clin Immunol, vol. 8:10, pp. 1-5, Jul. 2, 2012.
International Search Report and Written Opinion, US Patent and Trademark Office, Application No. PCT/US2014/065469, dated Feb. 12, 2015.

(Continued)

*Primary Examiner* — Blaine Lankford
(74) *Attorney, Agent, or Firm* — McCarter & English, LLC; Beverly W. Lubit

(57) ABSTRACT

Provided herein are methods of isolation and identification of post-natal hemogenic endothelial cells. Further provided are substantially purified populations of post-natal hemogenic endothelial cells, compositions of post-natal hemogenic endothelial cells, and methods to utilize hemogenic endothelial cells to regenerate the hematopoietic system in a subject.

25 Claims, 5 Drawing Sheets

(56) References Cited

OTHER PUBLICATIONS

Bordoni, V., et al. Hepatocyte-Conditioned Medium Sustains Endothelial Differentiation of Human Hematopoietic-Endothelial Progenitors. Hepatology 2007;45:1218-1228.
Pelosi, E. et al. Human Haemato-Endothelial Precursors: Cord Blood CD34+ Cells Produce Haemogenic Endothelium . PLoS One 7(12): e51109. doi:10.1371/journal.pone.0051109.

POST-NATAL HEMATOPOEITIC ENDOTHELIAL CELLS AND THEIR ISOLATION AND USE

CROSS-REFERENCE TO RELATED APPLICATIONS

This application claims priority to U.S. provisional application 61/956,194, filed Nov. 13, 2013, which is incorporated herein in its entirety.

BACKGROUND OF THE DISCLOSURE

During murine development, definitive hematopoietic stem cells (HSCs) originate in the dorsal aorta within the aorta-gonad-mesonephros (AGM) region (North, T. E. et al., *Immunity* 16:661-672 (2002); de Bruijn, M. F. et al., *EMBO J* 192:465-2474 (2000); Medvinsky, A. et al., *Cell* 86:897-906 (1996)). In vertebrates, including zebra fish, murine, and possibly human, HSCs are believed to emerge from the layer of hemogenic vascular cells lining the dorsal aorta floor and umbilical arteries (Zovein, A. C. et al., *Cell Stem Cell* 3:625-636 (2008); Boisset, J. C. et al., *Nature* 464:116-120 (2010); Bertrand, J. Y. et al., *Nature* 464:108-111 (2010); Kissa, K. et al., *Nature* 464:112-115 (2010)). Close association of developing endothelial cells (ECs) and HSC precursor cells in the embryo has led to an EC-hematopoietic transition theory of hematopoiesis (Zovein, A. C. et al., *Cell Stem Cell* 3:625-636 (2008)). Although it is known that HSCs and definitive erythroid/myeloid progenitors (EMPs) arise from multiple sites containing hemogenic ECs, it has been difficult to characterize the molecular programs driving the spontaneous ontogenetic transition of primitive hemogenic ECs to hematopoietic progenitors (Chen, M. J. et al., *Nature* 457:887-891 (2009); North, T. E. et al., *Cell* 137: 736-748 (2009)). However, it is commonly accepted that de-novo hematopoiesis does not occur post-natally.

It has been shown that during development of mammals, transitioning ECs/HECs are CD144$^+$CD45$^+$, but that expression of CD144 (also called VE-cadherin) was downregulated soon after the emergence of HSCs from embryonic HECs (North, T. E. et al., *Immunity* 16:661-672 (2002)). Kim et al. (*Blood* 106:903-905 (2005)) further identified CD144 expression as present on murine fetal liver HSCs at embryonic day E13.5, declining in expression at embryonic day E16.5, and absent in HSCs in liver and bone marrow by adulthood. CD144$^+$CD45$^+$ transitioning ECs/HECs are thus only known to be present in the embryo and not shown to be present after birth. Whether hemogenic endothelial cells exist anywhere within the organism after birth and whether post-natal endothelium is capable of giving rise to new HSCs and/or multi-potent hematopoietic progenitors are unknown.

Identification of cells with hemogenic potential in post-natal mammals would open up new possibilities for regeneration of the hematopoietic system.

BRIEF SUMMARY OF THE DISCLOSURE

Disclosed herein are methods of isolating post-natal hemogenic endothelial cells (HECs), by isolating CD144$^+$CD45$^+$ cells from a post-natal subject. Such HECs are capable of generating hematopoietic cells following transplantation into a recipient. In one embodiment, CD144$^+$CD45$^+$ cells are isolated from the liver, spleen, bone marrow, blood, umbilical cord, skin, kidney, muscle, or lung of a subject, preferably from the liver of the subject. HECs can be isolated to form a substantially pure population of CD144$^+$CD45$^+$ cells.

In other embodiments, the isolation step further includes selection of cells based on expression of at least one additional marker selected from CD180, chemokine C-X-C motif receptor 2 (CXCR2), chemokine C-X-C motif receptor 3 (CXCR3), chemokine C-X3-C motif receptor 1 (CX3CR1), chemokine C-C motif receptor 9 (CCR9), G protein-coupled receptor 141 (GPR141), G protein-coupled receptor 174 (GPR174), Signaling Lymphocyte Activation Molecule Family member 7 (SLAMF7), Signaling Lymphocyte Activation Molecule Family member 7 (SLAMF9), integrin alpha L (ITGAL), integrin alpha X (ITGAX), and membrane-spanning 4-domain, subfamily A, member 6D (MS4A6D).

This disclosure further contemplates compositions incorporating a substantially pure population of CD144$^+$CD45$^+$ post-natal HECs. In one embodiment, the HECs are autologous to a subject for whom administration of the composition is contemplated. In another embodiment, the HECs are allogeneic to a subject for whom administration of the composition is contemplated. In further embodiments, CD144$^+$CD45$^+$ post-natal HECs are in admixture with a pharmaceutically acceptable carrier, or in admixture with a suitable culture medium, or in admixture with a cryoprotective agent.

Further disclosed herein are methods of treatment for an immunodeficiency disorder, where the treatment includes administering a substantially pure population of CD144$^+$CD45$^+$ post-natal hemogenic endothelial cells to a subject in need thereof. The immunodeficiency disorder can be selected from a T-cell deficiency, a B-cell deficiency, a combined T-cell/B-cell deficiency, an antibody deficiency, a complement deficiency, leukemia, lymphoma, anemia, neutropenia, lymphopenia, lupus, and Wiskott-Aldrich syndrome. The immunodeficiency disorder can arise or result from administration of an immunosuppressive or cytotoxic agent, or from infection with human immunodeficiency virus (HIV) or hepatitis.

Further disclosed herein are methods of identifying hemogenic endothelial cells (HECs) in a post-natal subject, involving identifying cells that are CD144$^+$CD45$^+$ in the subject. Methods of identifying HECs can further include identifying cells expressing at least one additional marker selected from CD180, chemokine C-X-C motif receptor 2 (CXCR2), chemokine C-X-C motif receptor 3 (CXCR3), chemokine C-X3-C motif receptor 1 (CX3CR1), chemokine C-C motif receptor 9 (CCR9), G protein-coupled receptor 141 (GPR141), G protein-coupled receptor 174 (GPR174), Signaling Lymphocyte Activation Molecule Family member 7 (SLAMF7), Signaling Lymphocyte Activation Molecule Family member 7 (SLAMF9), integrin alpha L (ITGAL), integrin alpha X (ITGAX), and membrane-spanning 4-domain, subfamily A, member 6D (MS4A6D).

DETAILED DESCRIPTION OF THE DISCLOSURE

Figure 1:
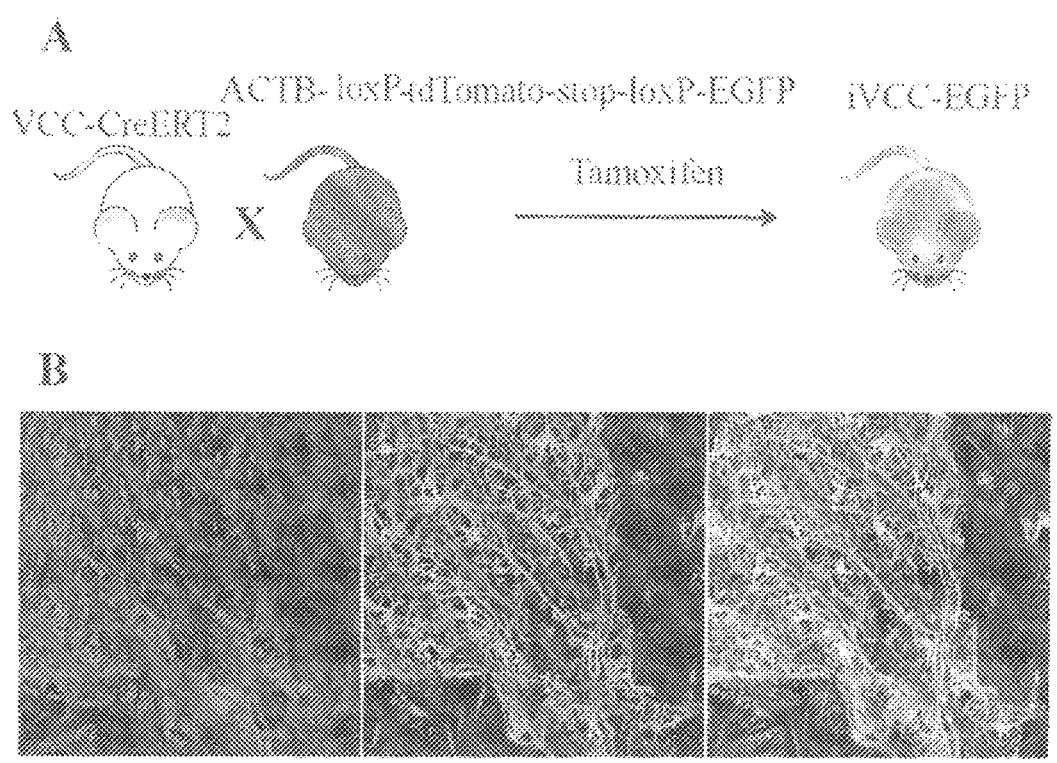
FIGS. 1A-1B. Temporally restricted genetic tracing of endothelial cells in post-natal mice. A. Transgenic mice with tamoxifen-inducible cre-recombinase CreERT2 under the control of endothelial specific VE-cadherin promoter (VCC-CreERT2 mice) were crossed with ACTB-loxp-tdTomato-STOP-loxp-EGFP reporter mice to generate inducible VCC-EGFP reporter mice (iVCC-EGFP). B. Tamoxifen injections induced EGFP expression in VE-cadherin expressing endothelial cells lining vascular beds. Left panel shows expression of tdTomato (red) in the skin of iVCC-EGFP mice. Middle panel shows EGFP expression (green) for the same area as shown in the left panel after tamoxifen induction (3 weeks post-natal). Right-hand panel shows overlap of the left and middle panels. Only the vasculature is showing EGFP expression.

This disclosure provides a previously unknown reservoir of hemogenic endothelial cells (HEC) in post-natal mammals that can give rise to hematopoietic cells, and surface markers that allows separation of HECs from other cell types. HECs are found in the endothelial cell layers of several organs and have the ability to reconstitute the immune system for the treatment of hematopoietic disorders.

Hemogenic Endothelial Cells

"Hemogenic endothelial cells" (HECs) are endothelial cells that have the capacity to generate hematopoietic cells, including hematopoietic stem cells. HECs as disclosed herein have the ability to engraft (establish residency) and provide long term repopulation of hematopoietic cells following transplantation into a recipient, such as an immuno-compromised subject. The disclosed HECs are also capable of subsequent engraftment from one recipient to one or more additional recipients, and thus retain the ability to regenerate the immune system. Capacity for long term engraftment (e.g., for 4 weeks, 8 weeks, 12 weeks, 16 weeks, or 20 weeks or longer post-transplantation) and secondary engraftment are highly desirable in a cell population for treatment of hematopoietic disorders.

HECs disclosed herein can be defined by expression of the markers CD45 (cluster of differentiation 45, also known as Protein tyrosine phosphatase, receptor type C or leukocyte common antigen/LCA) and CD144 (cluster of differentiation 144, also known as vascular-endothelial cadherin or VE-Cadherin). $CD144^+CD45^+$ expression defines HECs, and this combination of markers has not been previously identified in any cell type of a post-natal subject.

HECs can further optionally be defined by expression, in addition to $CD144^+CD45^+$, of one or more additional markers selected from CD180, chemokine C-X-C motif receptor 2 (CXCR2), chemokine C-X-C motif receptor 3 (CXCR3), chemokine C-X3-C motif receptor 1 (CX3CR1), chemokine C-C motif receptor 9 (CCR9), G protein-coupled receptor 141 (GPR141), G protein-coupled receptor 174 (GPR174), Signaling Lymphocyte Activation Molecule Family member 7 (SLAMF7), Signaling Lymphocyte Activation Molecule Family member 7 (SLAMF9), integrin alpha L (ITGAL), integrin alpha X (ITGAX), and membrane-spanning 4-domain, subfamily A, member 6D (MS4A6D). Preferably, the cells show positive expression of one or more of these additional markers. HECs can be defined by expression of 1, 2, 3, 4, 5, 6, 7, 8, or all of these additional markers, in addition to $CD144^+CD45^+$ expression. In one embodiment, HECs are defined as $CD144^+CD45^+SLAMF9^+CXCR1^+$ cells.

HECs have some characteristics of endothelial cells (ECs), for example, expression of the EC marker CD144 and optionally, expression of the EC marker CD31 (also known as platelet endothelial cell adhesion molecule-1 or PECAM-1). HECs can also be found in normal endothelial cell layers in organs and tissues, adjacent to ECs. However, unlike normal ECs, which adhere to gelatin-coated and other coated surfaces in culture, HECs do not adhere to coated surfaces, such as gelatin-coated surfaces, in culture.

"Hematopoeitic stem cells" (HSCs) are cells that can generate hematopoietic cells (HCs). HSCs can be defined by expression of $Lin^-CD34^+CD38^-CD90^+CD45RA^-CD45^+$ (human HSCs) and $Lin^-cKit^+Sca1^+Flk2^-CD34^-Slamf1^+$ (murine HSCs).

"Hematopoeitic cells" encompass myeloid lineage cells, which include erythrocytes, monocytes, macrophages, megakaryocytes, myeloblasts, dendritic cells, and granulocytes (basophils, neutrophils, eosinophils, and mast cells); and lymphoid lineage cells, which include T lymphocytes/T cells, B lymphocytes/B cells, and natural killer cells. The HECs disclosed herein have the ability to generate HSCs and HCs including myeloid lineage cells and lymphoid lineage cells.

HECs have some characteristics of HSCs, for example, HECs can generate new HCs. However, unlike HCs and HSCs, HECs have not been found to expand under typical conditions for culturing HSCs using standard concentrations of hematopoietic cytokines, such as SCF (stem cell factor), TPO (thrombopoietin), FLT3L (Flt-3 ligand), and IL-3 (interleukin-3).

Identifying HECs

Disclosed herein are methods of identifying post-natal hemogenic endothelial cells (HECs) in a subject. The methods involve identifying $CD144^+CD45^+$ cells in a post-natal subject. The methods can further involve identifying cells that are $CD144^+CD45^+$ and also show expression of one or more additional markers, in particular expression of one, two, three, four, five, six, seven, eight, or more markers selected from CD180, CXCR2, CXCR3, CX3CR1, CCR9, GPR141, GPR174, SLAMF7, SLAMF9, ITGAL, ITGAX, and MS4A6D. Identification can be in vitro or in vivo, for example, using antibodies or antigen-binding fragments thereof that bind to cell surface markers, conjugated to an imaging moiety such as a fluorescent or magnetic agent, a radioisotope, or other suitable imaging agent.

In one embodiment, a specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection.

Isolation of HECs

Disclosed herein are methods of isolating post-natal HECs. The methods involve isolating $CD144^+CD45^+$ cells from at least one tissue of a post-natal subject. The methods can further involve isolating cells that are $CD144^+CD45^+$ and also show expression of one or more additional markers, in particular expression of one, two, three, four, five, six, seven, eight, or more markers selected from CD180, CXCR2, CXCR3, CX3CR1, CCR9, GPR141, GPR174, SLAMF7, SLAMF9, ITGAL, ITGAX, and MS4A6D.

The terms "isolated" and "purified" are used interchangeably herein to refer to a material that is substantially or essentially removed from or concentrated in its natural environment. For example, a cell is isolated if it is substantially removed from other endogenous cell types, tissues, and materials which the cell would normally be found in proximity to in a subject. Methods for purification and isolation of cell types according to expression of cell-surface markers are documented methodologies. A "substantially isolated" cell or cell population is a cell or cell population that is at least 50%, 60%, 70%, 80%, 85%, 90%, 95%, 98%, or 99% or more isolated from other cell types, tissues, or materials found in the tissue of a subject. Also, a cell or cell population is "substantially purified" when at least 50%, 60%, 70%, 80%, 85%, 90%, 95%, 98%, or 99% or more of the cells in a cell sample express the cell-surface markers of interest.

HECs can be isolated from tissues and organs throughout the body including, but not limited to, the liver, spleen, bone marrow, blood, umbilical cord, skin, kidney, muscle, or lung. Preferred tissues include liver, blood, umbilical cord, and skin. In one embodiment, HECs are isolated from a biological sample obtained by biopsy of a tissue or organ. In another embodiment, HECs are isolated from a blood or plasma sample. Autologous HECs are isolated from the same subject to whom the HECs are to be administered. Allogeneic HECs are isolated from at least one individual of the same species as the subject to whom the HECs are to be administered. Xenogeneic HECs are isolated from at least one individual of a different species from the subject to whom the HECs are to be administered. Non-autologous HECs (that is, allogeneic or xenogeneic HECs) can be derived from pre-natal, post-natal, or post-mortem tissues or organs. Preferred HECs are autologous. Preferred non-autologous HECs are allogeneic post-natal HECs. The most preferred HECs are autologous and post-natal.

As a first step, HECs are isolated from a tissue, organ, or biological sample, according to $CD144^+CD45^+$ expression, optionally in combination with one or more additional markers as disclosed above. Methods to isolate or separate cells according to expression of cell surface markers include: fluorescence activated cell sorting by the use of e.g. antibodies or fragments thereof directed to CD144 and CD45, and optionally using additional antibodies or fragments thereof directed to additional markers; magnetic separation, using e.g. antibody-coated magnetic beads; affinity chromatography using antibodies or fragments thereof; "panning" with antibodies or fragments thereof attached to a solid matrix, e.g., a plate or other solid matrix; or other techniques as are known and used in the art for separation of cells based on cell surface marker expression. In preferred embodiments, fluorescence activated cell sorting or magnetic separation is used to isolate HECs from non-HECs.

Isolation of HECs generates a substantially pure population of $CD144^+CD45^+$ cells. As defined herein, a "substantially pure population" of $CD144^+CD45^+$ cells means more than 50%, more than 60%, more than 70%, more than 75%, more than 80%, more than 85%, more than 90%, more than 95%, more than 98%, more than 99%, or even 100% of the cells following the isolation/separation step are $CD144^+CD45^+$.

Culture, Maintenance, and Cryopreservation of HECs

Following isolation, HECs can be maintained in culture for up to one week with standard human/mammalian cell culture media, such as RPMI1640, Minimal Essential Medium (MEM), or Dulbecco's Modified Eagle Medium (DMEM) (each of these and similar media available for example through Gibco/Life Technologies), supplemented with serum, such as 5-30%, preferably 10-25%, most preferably 20% serum such as fetal bovine/calf serum (FBS or FCS), and one or more growth supplements for endothelial cells, such as Endothelial Cell Growth Supplement (ECGS) at 2-200 µg/mL. In a preferred embodiment, HECs are maintained in RPMI 1640 media with 20% FCS and ECGS at 2-200 µg/ml for 1 to 7 days, preferably between 4 to 72 hours or 1, 2, 3, or 4 days, and then frozen for storage until needed using the cryopreservation methods disclosed herein.

Culture of HECs requires particular conditions, as these cells survive and proliferate poorly or not at all using standard methods for culturing endothelial or hematopoietic cells. Preferred culture conditions can include culturing HECs on a layer of feeder cells, such as bone-marrow stroma or fetal/embryonic organ specific (liver) fibroblasts.

Isolated HECs can be cryopreserved using techniques known in the art for cell cryopreservation. HECs can be frozen for storage, either directly after isolation, or following maintenance in culture conditions as described above, or after proliferation in culture. Accordingly, in one embodiment, HECs can be removed from a subject and frozen, until such time that it is determined that a subject is in need of treatment for an immunodeficiency disorder, at which point the HECs can be thawed and transplanted back into the subject (for autologous transplantation) or thawed and transplanted to a different subject in need of treatment (for non-autologous transplantation).

Isolated HECs can be prepared for cryogenic storage by addition of one or a combination of cryoprotective agents such as dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts. Addition of plasma or serum (e.g., to a concentration of 20-25%) may augment the protective effect of DMSO. HECs can be frozen, for example, in 60-40% growth media as disclosed above (e.g., RPMI 1650, MEM or DMEM) with 40-60% serum and 5-20% DMSO. In one embodiment, HECs are frozen in 50% growth media, 50% FCS (fetal calf serum) with 10% DMSO.

Isolated HECs admixed with cryoprotective agents should be cooled at a controlled rate for cryogenic storage. Different cryoprotective agents and different cell types have different optimal cooling rates. Considerations and procedures for the manipulation, cryopreservation, and long-term storage of HSC sources are known in the art. Considerations in the thawing and reconstitution of frozen cell sources are also known in the art.

Isolated and Purified Populations of HECs and Compositions Thereof

Further encompassed by the subject disclosure is a substantially pure population of $CD144^+CD45^+$ post-natal hemogenic endothelial cells, wherein more than 80%, more than 85%, more than 90%, more than 91%, more than 92%, more than 93%, more than 94%, more than 95%, more than 96%, more than 97%, more than 98%, more than 99%, more than 99.5%, or even 100% of the cells following the isolation/separation step are $CD144^+CD45^+$.

Also contemplated are compositions that include a substantially pure population of $CD144^+CD45^+$ post-natal HECs. In one embodiment, the substantially pure population of $CD144^+CD45^+$ post-natal HECs is included in a composition with at least one cryoprotective agent, such as disclosed above. The cells in this composition can be in a frozen or unfrozen state. In another embodiment, the substantially pure population of $CD144^+CD45^+$ post-natal HECs is included in a composition with a suitable culture medium, such as the culture media disclosed for maintenance of HECs in vitro. In another embodiment, the substantially pure population of $CD144^+CD45^+$ post-natal HECs is included in a composition with a pharmaceutically acceptable carrier suitable for administration to a subject.

As used herein the phrase "pharmaceutically acceptable" means the carrier, or vehicle, does not cause an adverse reaction when administered to a mammal. Such carriers are non-toxic and do not create an inflammatory or anergic response in the body. Pharmaceutically acceptable carriers for practicing the invention include well known components such as, for example, culture media and phosphate buffered saline. Additional pharmaceutically acceptable carriers and their formulations are well-known and generally described in, for example, Remington's Pharmaceutical Science (18th Ed., ed. Gennaro, Mack Publishing Co., Easton, Pa., 1990) and the Handbook of Pharmaceutical Excipients (4th ed., Ed. Rowe et al. Pharmaceutical Press, Washington, D.C.), each of which is incorporated by reference.

Examples of compositions of $CD144^+CD45^+$ post-natal hemogenic endothelial cells include liquid preparations for parenteral, subcutaneous, intradermal, intramuscular, or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavorings, colors, and the like, depending upon the route of administration and the preparation desired.

A prefilled injection vial, ampoule or infusion bag of in unit dose form, encompassing the isolated HECs is also provided. The injection vial, ampoule or infusion bag can include $1 \times 10^4$ to $1 \times 10^{10}$ HECs, $1 \times 10^5$ to $1 \times 10^9$ HECs, or $1 \times 10^6$ to $1 \times 10^8$ HECs.

The compositions of the present invention are administered in a manner compatible with the dosage formulation, and in a therapeutically effective amount. The quantity to be administered depends, for instance, on the subject and debilitation to be treated, capacity of the subject's organ, cellular and immune system to accommodate the therapeutic composition, and the nature of the cell or tissue therapy, etc. Precise amounts of therapeutic composition required to be administered depend on the judgment of the practitioner and are peculiar to each individual. However, suitable dosages of the therapeutic composition of the present invention may range from about $1 \times 10^4$-$1 \times 10^{10}$ HECs per dose, or about $1 \times 10^5$-$1 \times 10^9$ HECs per dose, or about $1 \times 10^6$-$1 \times 10^8$ HECs per dose, depending on the route of administration. Suitable regimes for initial administration and follow on administration are also variable, but can include an initial administration followed by repeated doses at one or more hour, or day, intervals by a subsequent injection or other administration.

Methods of Treatment

Further provided herein are methods of treatment for an immunodeficiency disorder, the method including administering a composition with a substantially pure population of $CD144^+CD45^+$ HECs to a subject in need thereof. The HECs of the present invention can be used for reconstituting the full range of hematopoietic cells in an immunocompromised subject following therapies such as, but not limited to, radiation treatment and chemotherapy. Administration of the disclosed HECs, such as by infusion or transplantation into a subject, can augment or replace stem or progenitor cells of, for example, the liver, pancreas, kidney, lung, nervous system, muscular system, bone, bone marrow, thymus, or spleen. It is appreciated that it may be necessary to treat the host to reduce immunological rejection of the donor cells.

Preferred conditions treatable by the disclosed methods include immunodeficiency disorders characterized by an inadequate amount or activity of immune cells. The immunodeficiency disorder may be primary or secondary. In one embodiment, the immunodeficiency disorder is a primary immunodeficiency disorder selected from: a T-cell, B-cell, or combined T-cell/B-cell immunodeficiency, such as severe combined immunodeficiency (SCID); an antibody deficiency, such as agammaglobulinemia; a complement deficiency, such as lupus; leukemia; lymphoma; an anemia, such as severe aplastic anemia; neutropenia; lymphopenia; or any condition associated with immune deficiency, such as Wiskott-Aldrich syndrome. In another embodiment, the immunodeficiency disorder is a secondary immunodeficiency disorder associated with an infectious disease including human immunodeficiency virus (HIV) or hepatitis. In another embodiment, the immunodeficiency disorder is a secondary immunodeficiency disorder associated with the administration of an immunosuppressive agent, such as fluorouracil, vincristine, cisplatin, oxoplatin, methotrexate, 3'-azido-3'-deoxythymidine, paclitaxel, doxetaxel, an anthracycline antibiotic, or mixtures thereof having a secondary immunosuppressive effect.

As used herein, the terms "subject" and "patient" are used interchangeably and refer to an animal, including mammals such as non-primates (e.g., cows, pigs, horses, cats, dogs, rats etc.) and primates (e.g., monkey and human). In particular embodiments, the subject is post-natal, that is, the subject is, for example, a newborn animal, a young animal, an adolescent animal, an adult animal, or an aged animal.

As used herein, "treatment" refers to clinical intervention in an attempt to alter the disease course of the individual or cell being treated. Therapeutic effects of treatment include without limitation, preventing recurrence of disease, alleviation of symptoms, diminishment of any direct or indirect pathological consequences of the disease, decreasing the rate of disease progression, amelioration or palliation of the disease state, and remission or improved prognosis. As used herein, the terms "therapeutically effective amount" and "effective amount" are used interchangeably to refer to an amount of a composition of the invention that is sufficient to treat the immunological condition.

With respect to administering the HECs provided herein to a patient, an effective amount of cells may range from as few as several hundred or fewer to as many as several million or more. It will be appreciated that the number of HECs to be administered will vary depending on the specifics of the disorder to be treated, including but not limited to size or total volume to be treated, as well as the needs and condition of the recipient, among other factors familiar to the medical professional. In some embodiments, between $10^4$ and $10^{10}$ cells per 100 kg person are administered or transplanted into the subject or individual. HECs provided herein can be administered or transplanted, for example, by intravenous infusion or by direct grafting, using methods known in the art.

In one embodiment, HECs are used to augment or replace bone marrow cells in bone marrow transplantation. Human autologous and allogenic bone marrow transplantations are currently used as therapies for diseases such as leukemia and lymphoma. The drawback of these procedures, however, is that a large amount of donor bone marrow must be removed to insure that there are enough cells for engraftment. The present invention reduces or eliminates the need for large bone marrow donation, by substituting or supplementing a marrow donation with HECs for transplantation into a recipient. The HECs can be autologous to the subject, or allogeneic to the subject, or xenogeneic to the subject.

In another embodiment, HECs are administered to the bloodstream by infusion.

In another embodiment, HECs are administered by transplantation to an organ, such as the liver, spleen, kidney, lung, eye, central nervous system, muscle, skin, bone, ovary, testis, heart, blood vessel, intestine, or lymph node.

In some embodiments, a single administration of cells is provided. In other embodiments, multiple administrations are used. Multiple administrations can be provided over periodic time periods such as an initial treatment regime of 3 to 7 consecutive days, and then repeated at other times.

Further contemplated are methods involving co-administration, that is, administration of a composition of the invention before, after, or contemporaneously with administration of a treatment that may deplete the immune system or immune response of a subject. Such methods involve administering a composition with HECs to a subject before, during, and/or after treatments including cancer treatment and treatment with immunosuppressive agents. The term "cancer treatment" includes administration of any cancer agent including radioactive isotopes and cytotoxic agents. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, and glucocorticoid and other chemotherapeutic agents. Examples of immunosuppressive agents include cyclosporine, GAD65 antibodies, fluorouracil, cisplatin, oxoplatin, methotrexate, 3'-azido-3'-deoxythymidine, paclitaxel, doxetaxel, an anthracycline antibiotic, or mixtures thereof having a secondary immunosuppressive effect. Several cytotoxic agents as indicated herein are also immunosuppressive agents.

The present disclosure is further illustrated by the following non-limiting examples.

EXAMPLES

Example 1. Generation of Mice with Inducible Expression of Cre-Recombinase Under Control of the CD144 Promoter Transgenic mice with tamoxifen-inducible Cre-recombinase CreERT2 under the control of endothelial specific VE-cadherin promoter (VCC-CreERT2 mice) (Pitulescu M. et al., *Nat. Protoc.* 5:1518-1534 (2010)) were crossed with ACTB-loxp-tdTomato-STOP-loxp-EGFP reporter mice (Muzumdar M. et al., *Genesis* 45:593-605 (2007)) (FIG. 1A). The ACTB-loxp-tdTomato-STOP-loxp-EGFP reporter consists of a chicken β-actin core promoter with a CMV enhancer (pCA) driving a loxP flanked coding sequence of membrane-targeted tandem dimer Tomato (tdTomato) resulting in membrane localized tdTomato (a red fluorescent protein) expression. In progeny from the cross (inducible VCC-EGFP reporter mice or "iVCC-EGFP mice"), injection of tamoxifen induces Cre-recombinase expression in cells in which VE-cadherin/CD144 expression is activated. Cre-recombinase mediates intra-chromosomal recombination, causing excision of tdTomato at the loxP sites (and loss of red fluorescence) in CD144 expressing cells. Excision of tdTomato allows the pCA promoter to drive expression of membrane-targeted enhanced green fluorescent protein, thus identifying cells in which CD144 expression is turned on subsequent to tamoxifen induction by green fluorescence. This allowed tracing of endothelial cells in a temporally restricted manner.

iVCC-EGFP mice were induced with tamoxifen at 4 weeks post-natally (mice are considered to be adult mice at weaning age of 3 weeks). As seen in FIG. 1B, the tamoxifen injections induced EGFP expression in VE-cadherin expressing cells. The left panel of FIG. 1B shows expression of tdTomato (red) in the skin of iVCC-EGFP mice. The middle panel shows EGFP expression (green) for the same area as shown in the left panel after tamoxifen induction. The right-hand panel shows the overlap of the left and middle panels. Only the vasculature is showing EGFP expression.

Example 2. Post-Natal $CD144^+CD45^+$ Cells Isolated from Liver, Spleen, Lung and Bone Marrow Analysis of several organs harvested from iVCC-EGFP mice induced with tamoxifen at 4 weeks post-natally revealed the presence of $CD144^+CD45^+$ endothelial cells in the lung, liver, spleen, and bone marrow (FIG. 2A).

Figure 2:
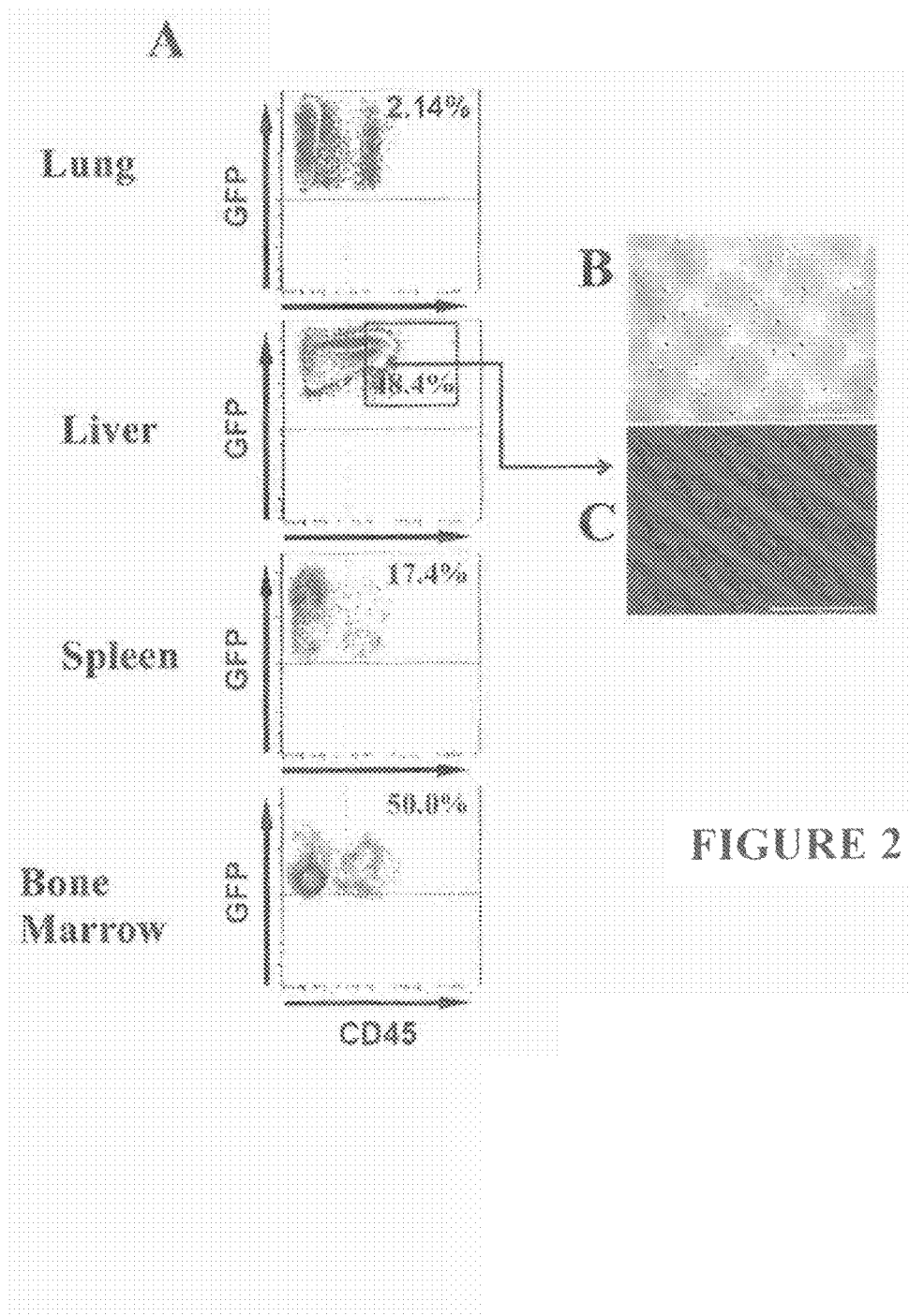
FIGS. 2A-2C. $CD144^+CD45^+$ cells are found in tissues including liver, spleen, lung and bone marrow. iVCC-EGFP mice were induced with tamoxifen at 4 weeks post-natally. A. Analysis of several organs harvested from the induced mice revealed the presence of $CD144^+CD45^+$ endothelial cells in the lung, liver, spleen, and bone marrow. B. Brightfield image of sorted $CD144^+CD45^+$ cells. Scale bar, 400 µm. C. Green fluorescent image of same field of view as B, showing that $CD144^+CD45^+$ cells are also $GFP^+$. As seen in B. and C., the sorted cells did not attach to the plate surface, as regular endothelial cells would, and did not expand in the presence of hematopoietic cytokines, as regular hematopoietic progenitor cells would.

$CD144^+(GFP^+)CD45^+$ cells were sorted using standard techniques and plated for in vitro culture on gelatin-coated tissue culture plates using RPMI 1640 media, supplemented with 20% FCS, endothelial cell growth supplement (ECGS) at 2-200 µg/ml, and cytokines (SCF, TPO, FLT3L, IL6, and IL3) used for expansion of hematopoietic cells (FIG. 2B). The sorted cells did not attach to the gelatin-coated tissue culture surfaces, as regular endothelial cells would. The sorted cells also did not respond to or expand in the presence of hematopoietic cytokines, as regular hematopoietic progenitors would. This suggested that the isolated cells were not true endothelial cells, nor were they standard hematopoietic cells.

Example 3. $CD144^+CD45^+$ Endothelial Cells are Capable of Functional Reconstitution of the Hematopoietic System iVCC-EGFP mice were induced with tamoxifen at 6 weeks after birth (adult mice) and used for experiments two weeks post-induction. To label $CD144^+$ endothelial cells (arterial, venal, and capillary) mice were injected with anti-$CD144^+$ antibody peri-orbitally. Injected mice were sacrificed eight minutes post-injection to exclude labeling of the lymphatic vascular bed. This allowed double labeling of $CD144^+$ endothelial cells—genetically (by tamoxifen induction of VE-cadherin promoter driven expression of CRE recombinase) and by intra-vital staining of $CD144^+$ endothelial cells using anti $CD144^+$ antibodies. Liver was digested as described in Nolan D. J. et al., *Dev Cell* 26:204-219 (2013)). Briefly, liver was minced and incubated with Collagenase A (25 mg/ml), Dispase II (25 mg/ml), and DNase (250 mg/ml) (Roche) at 37° C. for 20-30 min to create a single cell suspension. Following digestion, cells were post-stained with anti-CD45 antibodies and antibodies to CD31, an additional endothelial specific surface marker.

Figure 3:
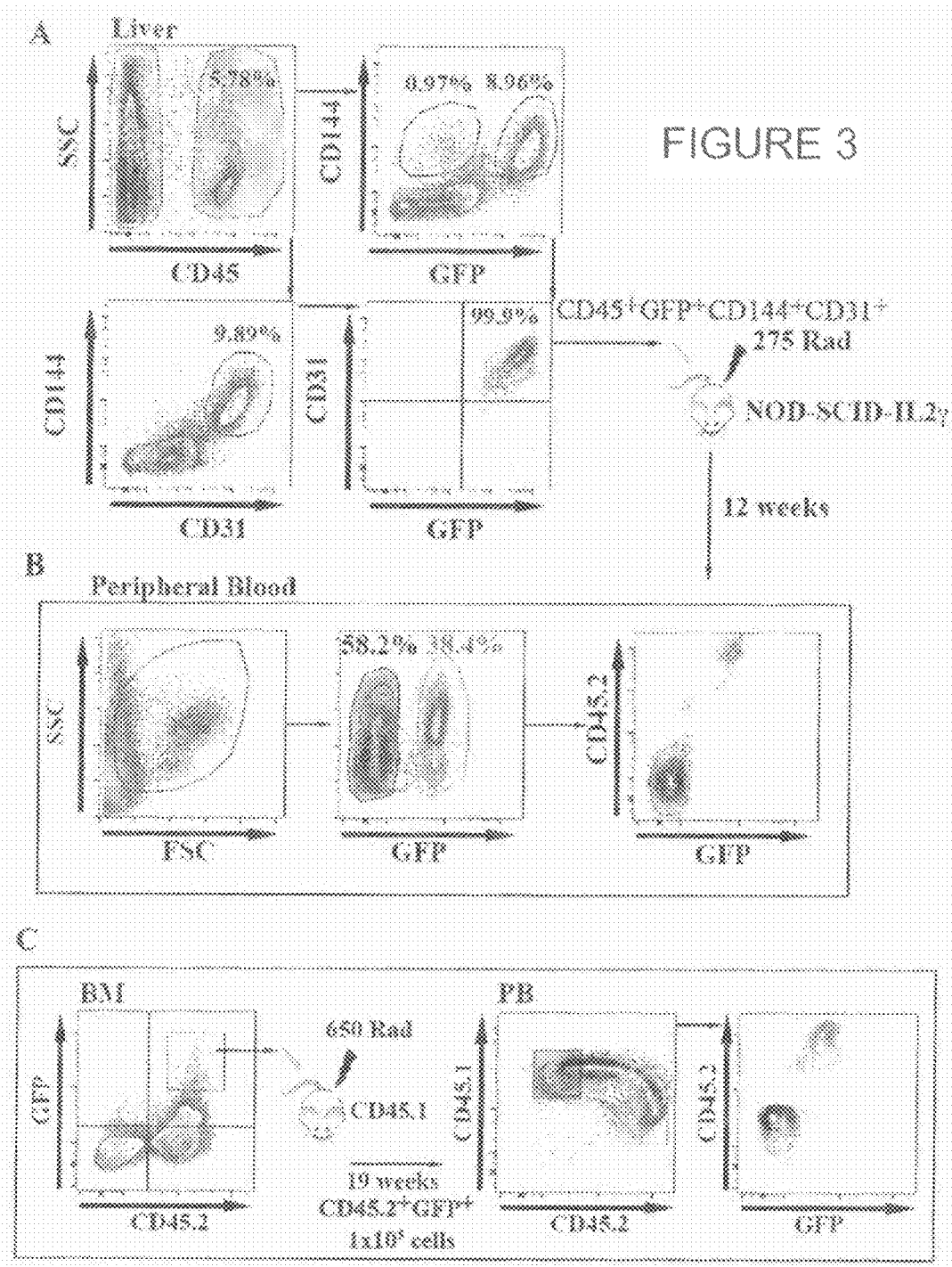
FIGS. 3A-3C. $CD144^+CD45^+$ endothelial cells are capable of functional reconstitution of the hematopoietic system. SSC, side scattered light. FSC, forward scattered light. BM, bone marrow. PB, peripheral blood. A. iVCC-EGFP mice were induced with tamoxifen at 6 weeks after birth (adult mice) and used for experiments two weeks post-induction. Mice were injected with anti-$CD144^+$ antibody and sacrificed eight minutes post-injection. Liver was digested and post-stained with antibodies against CD31 and CD45. $CD144^+GFP^+CD31^+CD45^+$ cells (red areas) were sorted using FACS and transplanted into immuno-compromised sub-lethally irradiated mice (NOD-SCID-IL2g ("NSG") mice). B. Twelve weeks post-transplantation, mice were tested for the presence of the donor cells in their peripheral blood. A significant portion of their peripheral blood (>35%) was composed of the donor $GFP^+CD45.2^+$ cells (green areas) (NSG mice express CD45.1 surface protein). C. $GFP^+CD45.2^+$ cells were isolated from the bone marrow of the primary recipients and used for secondary transplantations into a sub-lethally irradiated (650 RAD) CD45.1 expressing mice (non-NSG). Nineteen weeks post-transplantation, $CD45.2^+GFP^+$ cells (green areas) were detected in the peripheral blood of secondary recipients. These experiments prove that $CD144^+CD45^+$ endothelial cells are hemogenic (HEC) and capable of reconstitution of hematopoietic system when transplanted in vivo.

$CD144^+GFP^+CD31^+CD45^+$ cells were sorted using FACS and transplanted into imuno-compromised sub-lethally irradiated mice (NOD-SCID-IL2g or "NSG" mice) (FIG. 3A). Twelve weeks post-transplantation, transplanted mice were tested for the presence of the donor cells in their peripheral blood. A significant portion of their peripheral blood (>35%) was composed of the donor $GFP^+CD45.2^+$ cells (NSG mice express CD45.1 surface protein) (FIG. 3B). $GFP^+CD45.2^+$ cells were isolated from the bone marrow of the primary recipients and used for secondary transplantations into a sub-lethally irradiated (650 RAD) CD45.1 expressing mice (non-NSG). Nineteen weeks post-transplantation $CD45.2^+GFP^+$ cells were detected in peripheral blood of secondary recipients. These experiments prove that $CD144^+CD45^+$ endothelial cells are hemogenic (HEC) and capable of reconstitution of the hematopoietic system when transplanted in vivo (FIG. 3C).

Example 4. Identification of Additional Markers that Distinguish HECs

To identify additional surface markers that could further delineate HECs from donor tissues including, but not limited to liver, whole-transcriptome profiles of $CD144^+CD45^+$ liver cells were compared to $CD144^+CD45^-$ liver cells. iVCC-EGFP mice were induced with tamoxifen at 6 weeks after birth (adult mice) and used for experiments two weeks post-induction. To label $CD144^+$ endothelial cells, mice were injected with anti-$CD144^+$ antibody peri-orbitally and sacrificed eight minutes post-injection. Liver was digested as described above and post-stained with anti-CD45 antibodies. $CD144^+GFP^+CD45^+$ and $CD144^+GFP^+CD45^-$ endothelial cells were sorted using FACS. Sorted cells were used for total RNA extraction. RNA was used for whole-transcriptome deep sequencing (RNA-Seq) (FIG. 4A).

Comparison of whole-transcriptome sequences of $CD144^+GFP^+CD45^+$ and $CD144^+GFP^+CD45^-$ endothelial cells revealed a separate cluster of genes (red dots in the FIG. 4B) overexpressed ($\log_2[CD144^+GFP^+CD45^+/CD144^+GFP^+CD45^-]>3$) in $CD144^+GFP^+CD45^+$ endothelial cells. Analysis of the overexpressed genes (FIG. 4B) revealed a set of additional cell-surface expressed proteins that can optionally be used to further define post-natal $CD144^+CD45^+$ HECs (FIG. 4C).

Figure 4:
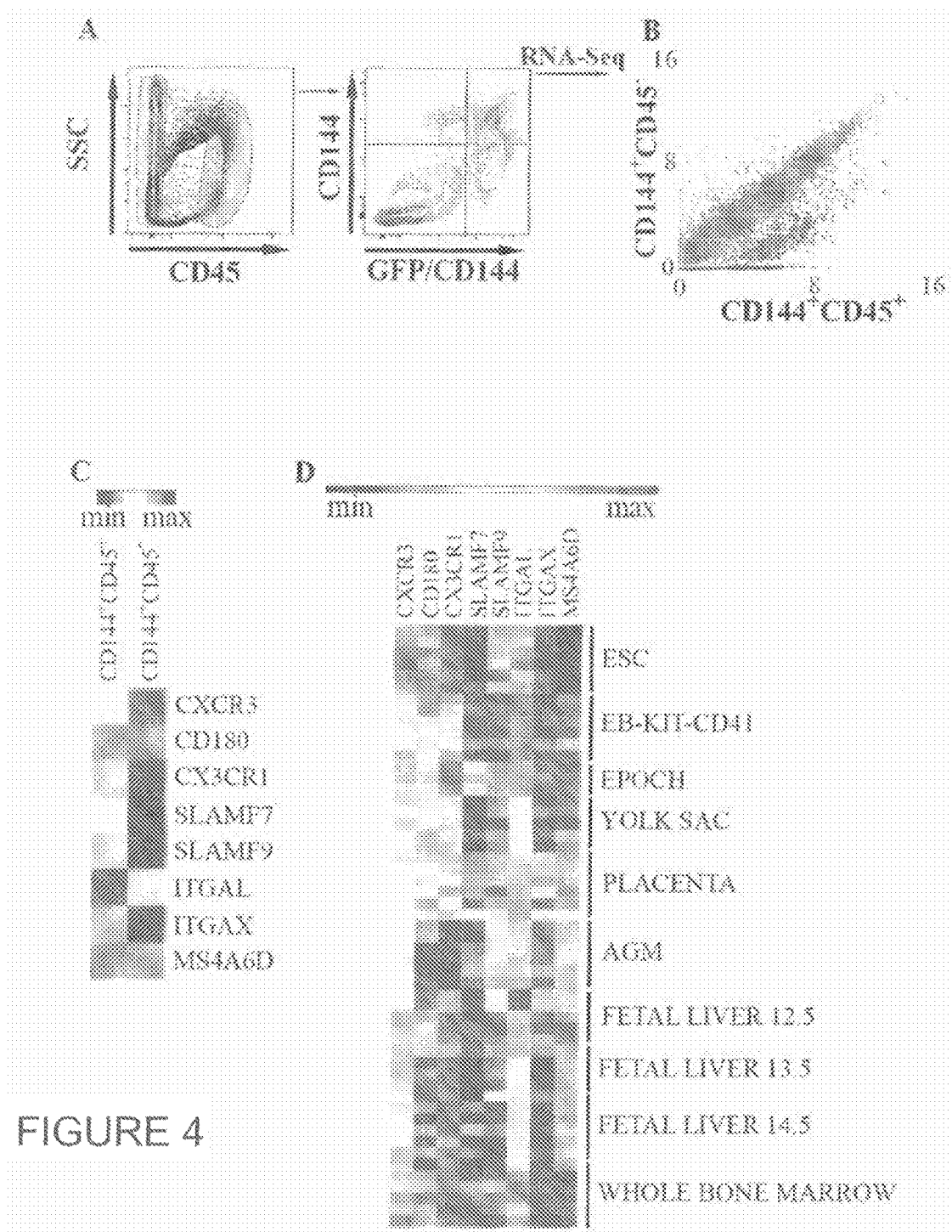
FIGS. 4A-4D. Whole-transcriptome deep sequencing reveals the hemogenic signature of $CD144^+CD45^+$ endothelial cells. A. Six week-old (adult) iVCC-EGFP mice were induced with tamoxifen and injected with anti-$CD144^+$ antibody two weeks after induction. Liver was digested and post-stained with anti-CD45 antibodies. $CD144^+GFP^+CD45^+$ (red gate in the left plot) and $CD144^+GFP^+CD45^-$ (blue gate in the left plot) endothelial cells were sorted using FACS (green gate in the middle plot). Sorted cells were used for total RNA extraction. RNA was used for whole-transcriptome deep sequencing (RNA-Seq). B. Comparison of whole-transcriptome sequences of $CD144^+GFP^+CD45^+$ and $CD144^+GFP^+CD45^-$ endothelial cells revealed a cluster of genes (red dots) that are upregulated ($\log_2[CD144^+GFP^+CD45^+/CD144^+GFP^+CD45^-]>3$) in $CD144^+GFP^+CD45^+$ endothelial cells. C. Analysis of the upregulated genes (minimum expression, blue; maximum expression, red) revealed a set of cell-surface expressed proteins (showing maximum expression in $CD144^+CD45^+$ cells, minimum expression in $CD144^+CD45^-$ cells) representing additional post-natal HEC surface markers. D. Analysis of the additional post-natal HEC surface markers revealed that these markers are typically upregulated in emerging hematopoietic cells/hemogenic endothelial cells during development in the areas known to be associated with definitive hematopoiesis, particularly AGM (showing maximum/red expression pattern).

Analysis of the novel post-natal HEC surface markers revealed that these markers are typically overexpressed in emerging hematopoietic cells/hemogenic endothelial cells during development in the areas known to be associated with definitive hematopoiesis, specifically, the placenta, AGM, and fetal liver (McKinney-Freeman S. et al., *Cell Stem Cell* 11:701-14 (2012)) (FIG. 4D).

Example 5. Isolation of $CD144^+CD45^+$ Cells from Human Liver

Figure 5:
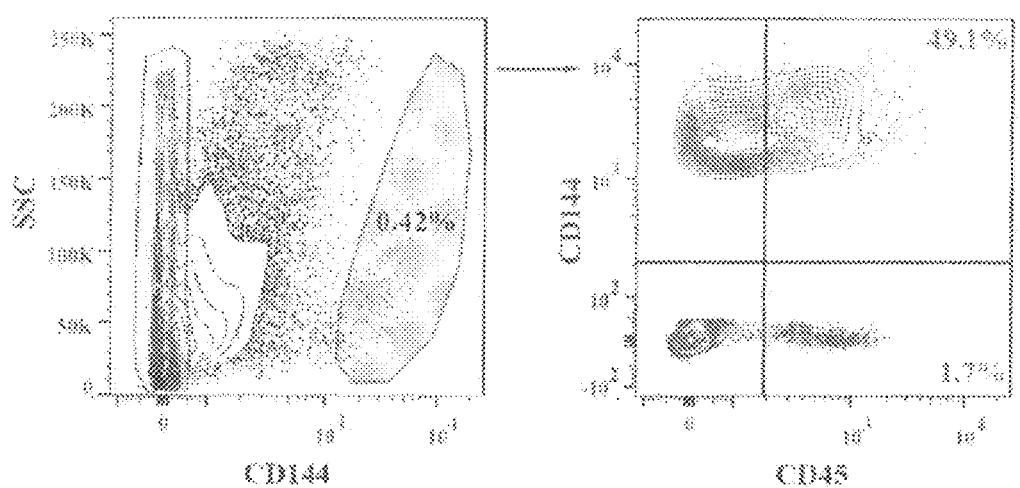
FIG. 5. $CD144^+CD45^+$ cells are found and isolated from a sample of human liver. A human liver biopsy was analyzed for the presence of $CD144^+CD45^+$ and $CD144^+CD45^-$ cells. A large portion of $CD144^+$ cells was also $CD45^+$ similar to mice livers. Red gate in the left graph corresponds to the red contour plot in the right graph. Blue gate in the left graph corresponds to the blue plot in the right graph.

The presence of $CD144^+CD45^+$ HECs was investigated in adult human liver. Human liver tissue samples from three unidentified adult individuals were analyzed for the presence of $CD144^+CD45^+$ and $CD144^+CD45^-$ cells. Surprisingly, a large portion of $CD144^+$ liver cells were also $CD45^+$, similar to mice livers (FIG. 5). This identifies HECs as present in adult humans.

What is claimed is:
1. A pharmaceutical composition comprising
   (a) a substantially pure population of $CD144^+/CD45^+$ post-natal hemogenic endothelial cells (HECs) derived from liver, spleen, bone marrow, skin, kidney, muscle, or lung tissue, and
   (b) a pharmaceutically acceptable carrier,
   wherein
   (i) the cells when cultured do not attach to gelatin-coated tissue culture surfaces, and do not expand in presence of hematopoietic cytokines;
   (ii) more than 50% of the post-natal HECs are $CD144^+/CD45^+$,

(iii) the post-natal HECs express one or more additional markers selected from the group consisting of CD180, chemokine C-X-C motif receptor 2 (CXCR2), chemokine C-X-C motif receptor 3 (CXCR3), chemokine C-X3-C motif receptor 1 (CX3CR1), chemokine C-C motif receptor 9 (CCR9), G protein-coupled receptor 141 (GPR141), G protein-coupled receptor 174 (GPR174), Signaling Lymphocyte Activation Molecule Family member 7 (SLAMF7), Signaling Lymphocyte Activation Molecule Family member 7 (SLAMF9), integrin alpha L (ITGAL), integrin alpha X (ITGAX), and membrane-spanning 4-domain, subfamily A, member 6D (MS4A6D); and (iv) biological activity of the post-natal HECs in vivo is characterized by:
 (1) functional reconstitution of hematopoietic cells following transplantation into a primary recipient; and
 (2) functional engraftment from the primary recipient to one or more secondary recipients the pharmaceutical composition being prepared by a method comprising:
 (1) obtaining a biologic tissue sample from the subject, wherein the tissue is selected from liver, spleen, bone marrow, skin, kidney, muscle, or lung of the subject;
 (2) dissociating the tissue sample mechanically;
 (3) enzymatically dissociating the tissue sample into a single-cell suspension;
 (4) sorting and selecting a population of cells expressing $CD144^+/CD45^+$ from the single cell suspension of (3);
 (5) plating the sorted cells expressing $CD144^+/CD45^+$ cells for in vitro culture on a non-adherent substrate, wherein the nonadherent substrate is a gelatin-coated tissue culture surface;
 (6) proliferating the HECs non-adherent on the nonadherent substrate in (5) by culturing the HECs on an adherent substrate excluding hematopoietic cytokines; and
 (7) combining the cells of step (6) or step (7) with a pharmaceutically acceptable carrier to form the pharmaceutical composition.

2. The composition of claim 1, wherein said HECs are autologous to the primary or secondary recipient for whom administration of said composition is contemplated.

3. The composition of claim 1, wherein said HECs are allogeneic to the primary or secondary recipient for whom administration of said composition is contemplated.

4. The composition of claim 1, wherein said composition comprises $CD144^+/CD45^+$ post-natal HECs in admixture with a culture medium.

5. The composition of claim 1, wherein said composition comprises $CD144^+/CD45^+$ post-natal HECs in admixture with a cryoprotective agent.

6. The pharmaceutical composition of claim 1, wherein more than 80% of the HECs are $CD144^+/CD45^+$.

7. The pharmaceutical composition of claim 1, wherein the sorting is by fluorescence activated cell sorting or magnetic separation.

8. The pharmaceutical composition of claim 1, wherein the primary or secondary recipient is an immunocompromised subject.

9. The pharmaceutical composition of claim 1, wherein the adherent substrate comprises feeder cells.

10. The pharmaceutical composition of claim 9, wherein the feeder cells are bone marrow stroma or fetal/embryonic organ-specific fibroblasts.

11. The pharmaceutical composition of claim 1, wherein a therapeutic amount of the pharmaceutical composition comprises a unit dose of from $1\times10^4$ to $1\times10^{10}$ post-natal HECs.

12. The pharmaceutical composition of claim 1, the method for preparing the composition comprising freezing the cells from step (6) for storage by cooling at a controlled rate in a medium comprising a cryoprotective agent, serum and growth medium.

13. A method of preparing a pharmaceutical composition comprising a substantially pure population of hemogenic endothelial cells (HECs) isolated from a tissue of a post-natal subject, comprising, in order
 (a) obtaining a biologic tissue sample from the subject, wherein the tissue is selected from liver, spleen, bone marrow, skin, kidney, muscle, or lung of the subject;
 (b) dissociating the tissue sample mechanically;
 (c) enzymatically dissociating the tissue sample into a single-cell suspension;
 (d) sorting and selecting a population of cells expressing $CD144^+/CD45^+$ from the single cell suspension of (c);
 (e) plating the sorted cells expressing $CD144^+/CD45^+$ cells for in vitro culture on a non-adherent substrate comprising a feeder cell layer;
 (f) proliferating HECs non-adherent on the nonadherent substrate in (e) by culturing the HECs on an adherent substrate;
 (g) optionally freezing the cells from step (f) for storage by cooling at a controlled rate in a medium comprising a cryoprotective agent, serum and a growth medium; and
 (h) combining the cells of step (f) or step (g) with a pharmaceutically acceptable carrier to form the composition, wherein the composition comprises isolated hemogenic endothelial cells of which more than 50% of the cells express $CD144^+/CD45^+$;
 wherein said HECs following administration to a recipient are effective to generate hematopoietic cells.

14. The method of claim 13, wherein the isolated HECs comprise a substantially pure population of $CD144^+/CD45^+$ post-natal cells.

15. The method of claim 13, wherein the method further comprises selecting cells based on expression of at least one additional marker selected from CD180, chemokine C-X-C motif receptor 2 (CXCR2), chemokine C-X-C motif receptor 3 (CXCR3), chemokine C-X3-C motif receptor 1 (CX3CR1), chemokine CC motif receptor 9 (CCR9), G protein-coupled receptor 141 (GPR141), G protein-coupled receptor 174 (GPR174), Signaling Lymphocyte Activation Molecule Family member 7 (SLAMF7), Signaling Lymphocyte Activation Molecule Family member 7 (SLAMF9), integrin alpha L (ITGAL), integrin alpha X (ITGAX), and membrane-spanning 4-domain, subfamily A, member 6D (MS4A6D).

16. The method according to claim 13, wherein the tissue sample is obtained by biopsy of the tissue.

17. The method according to claim 13, wherein the sorting in step (d) is by flow cytometry.

18. The method according to claim 13, wherein the feeder cell layer comprises bone marrow stroma or fetal/embryonic organ specific (liver) fibroblasts.

19. The method according to claim 13, wherein the cryoprotective agent is at least one selected from the group consisting of sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts.

20. A method for treating an immunodeficiency disorder, comprising administering to a subject in need thereof a therapeutic amount of a pharmaceutical composition containing a substantially pure population of hemogenic endothelial cells isolated from a tissue of a post-natal subject expressing CD144$^+$/CD45$^+$ and at least one additional marker selected from CD 180, chemokine C-X-C motif receptor 2 (CXCR2), chemokine C-X-C motif receptor 3 (CXCR3), chemokine C-X3-C motif receptor 1 (CX3CR1), chemokine C-C motif receptor 9 (CCR9), G protein-coupled receptor 141 (GPR141), G protein-coupled receptor 174 (GPR174), Signaling Lymphocyte Activation Molecule Family member 7 (SLAMF7), Signaling Lymphocyte Activation Molecule Family member 7 (SLAMF9), integrin alpha L (ITGAL), integrin alpha X (ITGAX), and membrane-spanning 4-domain, subfamily A, member 6D (MS4A6D) and a pharmaceutically acceptable carrier, wherein
   (a) the tissue is selected from liver, spleen, bone marrow, skin, kidney, muscle, or lung of the subject;
   (b) the composition comprises isolated HECs of which more than 50% of the cells express CD144$^+$/CD45$^+$; and
   (c) the composition is effective
      (i) to augment or replace stem or progenitor cells of liver, pancreas, kidney, lung, nervous system, muscular system, bone, bone marrow, thymus, spleen; or
      (ii) to reconstitute the hematopoietic system when transplanted in vivo.

21. The method of claim 20, wherein said immunodeficiency disorder is selected from a T-cell deficiency, a B-cell deficiency, a combined T-cell/B-cell deficiency, an antibody deficiency, a complement deficiency, leukemia, lymphoma, anemia, neutropenia, lymphopenia, lupus, and Wiskott-Aldrich syndrome.

22. The method of claim 20, wherein said immunodeficiency disorder results from administration of an immunosuppressive or cytotoxic agent.

23. The method of claim 20, wherein said immunodeficiency disorder results from infection with human immunodeficiency virus (HIV) or hepatitis.

24. The method according to claim 20, wherein
(a) the administering is by infusion or transplantation; or
(b) the administering by transplantation is a therapy for leukemia or lymphoma; or
(c) the immunodeficiency disorder is a primary immunodeficiency disorder selected from: a T-cell, B-cell, or combined T-cell/B-cell immunodeficiency, such as severe combined immunodeficiency (SCID); an antibody deficiency, such as agammaglobulinemia; a complement deficiency, such as lupus; leukemia; lymphoma; an anemia, such as severe aplastic anemia; neutropenia; lymphopenia; or a condition associated with immune deficiency, such as Wiskott-Aldrich syndrome; or
(d) the immunodeficiency disorder is a secondary immunodeficiency disorder associated with an infectious disease including human immunodeficiency virus (HIV) or hepatitis; or
(e) the administering includes administration of the composition to a subject before, during, and/or after treatment with an anticancer agent or treatment with immunosuppressive agents; or
(f) the immunodeficiency disorder is a secondary immunodeficiency disorder associated with administration of an immunosuppressive agent.

25. The method according to claim 24, wherein
(a) the anticancer agent is a cytotoxic agent selected from the group consisting of maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, and glucocorticoid and other chemotherapeutic agents; or
(b) the immunosuppressive agent is selected from the group consisting of cyclosporine, GAD65 antibodies, fluorouracil, cisplatin, oxoplatin, methotrexate, 3'-azido-3'-deoxythymidine, paclitaxel, doxetaxel, an anthracycline antibiotic, or mixtures thereof.

* * * * *

UNITED STATES PATENT AND TRADEMARK OFFICE
CERTIFICATE OF CORRECTION

Page 1 of 1

PATENT NO.         : 10,570,373 B2
APPLICATION NO.    : 15/032287
DATED              : February 25, 2020
INVENTOR(S)        : Vladislav M. Sandler It is certified that error appears in the above-identified patent and that said Letters Patent is hereby corrected as shown below:

On the Title Page

Item (54) and in the Specification, Column 1, Lines 1-3, In the title, replace Hematopoeitic with Hematopoietic.

In the Specification

Column 5, Line 8 and Column 5, Line 13: "Hematopoeitic" should be changed to "Hematopoietic".

Signed and Sealed this
Nineteenth Day of May, 2020

Andrei Iancu
*Director of the United States Patent and Trademark Office*